(12) United States Patent
Gleiman et al.

(10) Patent No.: US 10,470,767 B2
(45) Date of Patent: Nov. 12, 2019

(54) SURGICAL STAPLING INSTRUMENT HAVING ULTRASONIC ENERGY DELIVERY

(71) Applicant: Covidien LP, Mansfield, MA (US)

(72) Inventors: Seth Gleiman, Branford, CT (US); Anthony Ceniccola, Hamden, CT (US); Anne Nelson, Guilford, CT (US); Matthew Chowaniec, Middletown, CT (US); David Racenet, Killingsworth, CT (US); Jeffrey Schmitt, Trumbull, CT (US); Gerald Hodgkinson, Guilford, CT (US); Joshua Snow, Clinton, CT (US)

(73) Assignee: Covidien LP, Mansfield, MA (US)

( * ) Notice: Subject to any disclaimer, the term of this patent is extended or adjusted under 35 U.S.C. 154(b) by 1033 days.

(21) Appl. No.: 14/618,255

(22) Filed: Feb. 10, 2015

(65) Prior Publication Data

US 2016/0228145 A1 Aug. 11, 2016

(51) Int. Cl.
*A61B 17/072* (2006.01)
*A61B 17/32* (2006.01)
A61B 17/064 (2006.01)

(52) U.S. Cl.
CPC .. *A61B 17/07292* (2013.01); *A61B 17/07207* (2013.01); *A61B 17/320068* (2013.01);
(Continued)

(58) Field of Classification Search
CPC .............. A61B 17/068; A61B 17/0682; A61B 17/0684; A61B 17/0686; A61B 17/072;
(Continued)

(56) References Cited

U.S. PATENT DOCUMENTS

| 3,054,406 A | 9/1962 | Usher |
|---|---|---|
| 3,079,606 A | 3/1963 | Bobrov et al. |

(Continued)

FOREIGN PATENT DOCUMENTS

| CA | 2 667 434 A1 | 5/2008 |
|---|---|---|
| DE | 19924311 A1 | 11/2000 |

(Continued)

OTHER PUBLICATIONS

Extended European Search Report corresponding to EP 13 19 4995.0, completed Jun. 5, 2014 and dated Jun. 16, 2014; (5 pp).

(Continued)

*Primary Examiner* — Gloria R Weeks

(57) ABSTRACT

An end effector includes first and second jaws, first and second buttresses, and an ultrasonic blade. The first jaw includes a fastener cartridge having a first tissue contacting surface and a plurality of fasteners arranged in rows parallel to a longitudinal axis of the first jaw. The first buttress is attached to the first tissue contacting surface and the second buttress is attached to a second tissue contracting surface of the second jaw. The first and second jaws are movable relative to one another and are configured to grasp tissue therebetween. The ultrasonic is activatable to weld the first buttress to the second buttress and to subsequently cut the welded first and second buttresses and tissue grasped between the first and second jaws.

8 Claims, 6 Drawing Sheets

(52) U.S. Cl.
CPC .. *A61B 17/320092* (2013.01); *A61B 17/0643* (2013.01); *A61B 2017/07242* (2013.01); *A61B 2017/07285* (2013.01); *A61B 2017/320094* (2017.08); *A61B 2017/320095* (2017.08); *A61B 2017/320097* (2017.08)

(58) Field of Classification Search
CPC ...... A61B 17/07292; A61B 2017/0688; A61B 2017/07214; A61B 2017/07221; A61B 2017/07228; A61B 2017/07235; A61B 2017/07242; A61B 2017/0725; A61B 2017/07257; A61B 2017/07264; A61B 2017/07271; A61B 2017/07278; A61B 2017/07285; A61B 17/320068
USPC ......... 227/175.1–175.4, 176.1, 177.1, 178.1, 227/179.1, 180.1, 181.1, 182.1
See application file for complete search history.

(56) References Cited

U.S. PATENT DOCUMENTS

| | | |
|---|---|---|
| 3,124,136 A | 3/1964 | Usher |
| 3,364,200 A | 1/1968 | Ashton et al. |
| 3,490,675 A | 1/1970 | Green et al. |
| 3,499,591 A | 3/1970 | Green |
| 3,939,068 A | 2/1976 | Wendt et al. |
| 3,948,666 A | 4/1976 | Kitanishi et al. |
| 4,064,062 A | 12/1977 | Yurko |
| 4,166,800 A | 9/1979 | Fong |
| 4,282,236 A | 8/1981 | Broom |
| 4,347,847 A | 9/1982 | Usher |
| 4,354,628 A | 10/1982 | Green |
| 4,416,698 A | 11/1983 | McCorsley, III |
| 4,429,695 A | 2/1984 | Green |
| 4,452,245 A | 6/1984 | Usher |
| 4,605,730 A | 8/1986 | Shalaby et al. |
| 4,626,253 A | 12/1986 | Broadnax, Jr. |
| 4,655,221 A | 4/1987 | Devereux |
| 4,834,090 A | 5/1989 | Moore |
| 4,838,884 A | 6/1989 | Dumican et al. |
| 4,927,640 A | 5/1990 | Dahlinder et al. |
| 4,930,674 A | 6/1990 | Barak |
| 5,002,551 A | 3/1991 | Linsky et al. |
| 5,014,899 A | 5/1991 | Presty et al. |
| 5,040,715 A | 8/1991 | Green et al. |
| 5,057,334 A | 10/1991 | Vail |
| 5,065,929 A | 11/1991 | Schulze et al. |
| 5,162,430 A | 11/1992 | Rhee et al. |
| 5,205,459 A | 4/1993 | Brinkerhoff et al. |
| 5,263,629 A | 11/1993 | Trumbull et al. |
| 5,307,976 A | 5/1994 | Olson et al. |
| 5,312,023 A | 5/1994 | Green et al. |
| 5,314,471 A | 5/1994 | Brauker et al. |
| 5,318,221 A | 6/1994 | Green et al. |
| 5,324,775 A | 6/1994 | Rhee et al. |
| 5,326,013 A | 7/1994 | Green et al. |
| 5,332,142 A | 7/1994 | Robinson et al. |
| 5,344,454 A | 9/1994 | Clarke et al. |
| 5,392,979 A | 2/1995 | Green et al. |
| 5,397,324 A | 3/1995 | Carroll et al. |
| 5,410,016 A | 4/1995 | Hubbell et al. |
| 5,425,745 A | 6/1995 | Green et al. |
| 5,441,193 A | 8/1995 | Gravener |
| 5,441,507 A | 8/1995 | Wilk |
| 5,443,198 A | 8/1995 | Viola et al. |
| 5,468,253 A | 11/1995 | Bezwada et al. |
| 5,484,913 A | 1/1996 | Stilwell et al. |
| 5,503,638 A | 4/1996 | Cooper et al. |
| 5,514,379 A | 5/1996 | Weissleder et al. |
| 5,542,594 A | 8/1996 | McKean et al. |
| 5,543,441 A | 8/1996 | Rhee et al. |
| 5,549,628 A | 8/1996 | Cooper et al. |
| 5,550,187 A | 8/1996 | Rhee et al. |
| 5,575,803 A | 11/1996 | Cooper et al. |
| 5,653,756 A | 8/1997 | Clarke et al. |
| 5,683,809 A | 11/1997 | Freeman et al. |
| 5,688,270 A * | 11/1997 | Yates ............... A61B 17/07207 606/41 |
| 5,690,675 A | 11/1997 | Sawyer et al. |
| 5,702,409 A | 12/1997 | Rayburn et al. |
| 5,735,848 A * | 4/1998 | Yates ............... A61B 17/07207 227/175.1 |
| 5,752,965 A | 5/1998 | Francis et al. |
| 5,752,974 A | 5/1998 | Rhee et al. |
| 5,762,256 A | 6/1998 | Mastri et al. |
| 5,766,188 A | 6/1998 | Igaki |
| 5,769,892 A | 6/1998 | Kingwell |
| 5,782,396 A | 7/1998 | Mastri et al. |
| 5,799,857 A | 9/1998 | Robertson et al. |
| 5,810,855 A | 9/1998 | Rayburn et al. |
| 5,814,057 A | 9/1998 | Oi et al. |
| 5,819,350 A | 10/1998 | Wang |
| 5,833,695 A | 11/1998 | Yoon |
| 5,843,096 A | 12/1998 | Igaki et al. |
| 5,874,500 A | 2/1999 | Rhee et al. |
| 5,895,412 A | 4/1999 | Tucker |
| 5,895,415 A | 4/1999 | Chow et al. |
| 5,902,312 A | 5/1999 | Frater et al. |
| 5,908,427 A | 6/1999 | McKean et al. |
| 5,915,616 A | 6/1999 | Viola et al. |
| 5,931,847 A | 8/1999 | Bittner et al. |
| 5,964,774 A | 10/1999 | McKean et al. |
| 5,997,895 A | 12/1999 | Narotam et al. |
| 6,004,335 A * | 12/1999 | Vaitekunas ...... A61B 17/07207 227/180.1 |
| 6,019,791 A | 2/2000 | Wood |
| 6,030,392 A | 2/2000 | Dakov |
| 6,032,849 A | 3/2000 | Mastri et al. |
| 6,045,560 A | 4/2000 | McKean et al. |
| 6,063,097 A | 5/2000 | Oi et al. |
| 6,080,169 A | 6/2000 | Turtel |
| 6,093,557 A | 7/2000 | Pui et al. |
| 6,099,551 A | 8/2000 | Gabbay |
| 6,149,667 A | 11/2000 | Hovland et al. |
| 6,152,943 A | 11/2000 | Sawhney |
| 6,155,265 A | 12/2000 | Hammerslag |
| 6,156,677 A | 12/2000 | Brown Reed et al. |
| 6,165,201 A | 12/2000 | Sawhney et al. |
| 6,179,862 B1 | 1/2001 | Sawhney |
| 6,193,129 B1 * | 2/2001 | Bittner ............... A61B 17/1114 227/180.1 |
| 6,210,439 B1 | 4/2001 | Firmin et al. |
| 6,214,020 B1 | 4/2001 | Mulhauser et al. |
| 6,241,139 B1 | 6/2001 | Milliman et al. |
| 6,258,107 B1 | 7/2001 | Balazs et al. |
| 6,267,772 B1 | 7/2001 | Mulhauser et al. |
| 6,273,897 B1 | 8/2001 | Dalessandro et al. |
| 6,280,453 B1 | 8/2001 | Kugel et al. |
| 6,299,631 B1 | 10/2001 | Shalaby |
| 6,309,569 B1 | 10/2001 | Farrar et al. |
| 6,312,457 B1 | 11/2001 | DiMatteo et al. |
| 6,312,474 B1 | 11/2001 | Francis et al. |
| 6,325,810 B1 | 12/2001 | Hamilton et al. |
| 6,399,362 B1 | 6/2002 | Pui et al. |
| 6,436,030 B2 | 8/2002 | Rehil |
| 6,454,780 B1 | 9/2002 | Wallace |
| 6,461,368 B2 | 10/2002 | Fogarty et al. |
| 6,500,777 B1 | 12/2002 | Wiseman et al. |
| 6,503,257 B2 | 1/2003 | Grant et al. |
| 6,514,283 B2 | 2/2003 | DiMatteo et al. |
| 6,514,534 B1 | 2/2003 | Sawhney |
| 6,517,566 B1 | 2/2003 | Hovland et al. |
| 6,551,356 B2 | 4/2003 | Rousseau |
| 6,566,406 B1 | 5/2003 | Pathak et al. |
| 6,590,095 B1 | 7/2003 | Schleicher et al. |
| 6,592,597 B2 | 7/2003 | Grant et al. |
| 6,605,294 B2 | 8/2003 | Sawhney |
| 6,627,749 B1 | 9/2003 | Kumar |
| 6,638,285 B2 | 10/2003 | Gabbay |
| 6,652,594 B2 | 11/2003 | Francis et al. |
| 6,656,193 B2 | 12/2003 | Grant et al. |
| 6,656,200 B2 | 12/2003 | Li et al. |
| 6,669,735 B1 | 12/2003 | Pelissier |

(56) References Cited

U.S. PATENT DOCUMENTS

| | | | |
|---|---|---|---|
| 6,673,093 B1 | 1/2004 | Sawhney | |
| 6,677,258 B2 | 1/2004 | Carroll et al. | |
| 6,685,714 B2 | 2/2004 | Rousseau | |
| 6,702,828 B2 | 3/2004 | Whayne | |
| 6,703,047 B2 | 3/2004 | Sawhney et al. | |
| 6,704,210 B1* | 3/2004 | Myers | A61B 17/07207 349/150 |
| 6,723,114 B2 | 4/2004 | Shalaby | |
| 6,726,706 B2 | 4/2004 | Dominguez | |
| 6,736,823 B2 | 5/2004 | Darois et al. | |
| 6,736,854 B2 | 5/2004 | Vadurro et al. | |
| 6,746,458 B1 | 6/2004 | Cloud | |
| 6,746,869 B2 | 6/2004 | Pui et al. | |
| 6,764,720 B2 | 7/2004 | Pui et al. | |
| 6,773,458 B1 | 8/2004 | Brauker et al. | |
| 6,818,018 B1 | 11/2004 | Sawhney | |
| 6,821,273 B2* | 11/2004 | Mollenauer | A61B 17/07207 606/142 |
| 6,896,684 B2 | 5/2005 | Monassevitch et al. | |
| 6,927,315 B1 | 8/2005 | Heinecke et al. | |
| 6,939,358 B2 | 9/2005 | Palacios et al. | |
| 6,946,196 B2 | 9/2005 | Foss | |
| 6,959,851 B2 | 11/2005 | Heinrich | |
| 7,009,034 B2 | 3/2006 | Pathak et al. | |
| 7,060,087 B2 | 6/2006 | DiMatteo et al. | |
| 7,087,065 B2 | 8/2006 | Ulmsten et al. | |
| 7,108,701 B2 | 9/2006 | Evens et al. | |
| 7,128,253 B2 | 10/2006 | Mastri et al. | |
| 7,128,748 B2 | 10/2006 | Mooradian et al. | |
| 7,141,055 B2 | 11/2006 | Abrams et al. | |
| 7,147,138 B2 | 12/2006 | Shelton, IV | |
| 7,160,299 B2* | 1/2007 | Baily | A61B 18/1445 128/898 |
| 7,232,449 B2 | 6/2007 | Sharkawy et al. | |
| 7,241,300 B2 | 7/2007 | Sharkawy et al. | |
| 7,247,338 B2 | 7/2007 | Pui et al. | |
| 7,279,322 B2 | 10/2007 | Pui et al. | |
| 7,307,031 B2 | 12/2007 | Carroll et al. | |
| 7,311,720 B2 | 12/2007 | Mueller et al. | |
| 7,347,850 B2 | 3/2008 | Sawhney | |
| 7,377,928 B2 | 5/2008 | Zubik et al. | |
| 7,434,717 B2 | 10/2008 | Shelton, IV et al. | |
| 7,438,209 B1 | 10/2008 | Hess et al. | |
| 7,498,063 B2 | 3/2009 | Pui et al. | |
| 7,547,312 B2 | 6/2009 | Bauman et al. | |
| 7,559,937 B2 | 7/2009 | de la Torre et al. | |
| 7,594,921 B2 | 9/2009 | Browning | |
| 7,595,392 B2 | 9/2009 | Kumar et al. | |
| 7,604,151 B2 | 10/2009 | Hess et al. | |
| 7,611,494 B2 | 11/2009 | Campbell et al. | |
| 7,649,089 B2 | 1/2010 | Kumar et al. | |
| 7,662,801 B2 | 2/2010 | Kumar et al. | |
| 7,665,646 B2 | 2/2010 | Prommersberger | |
| 7,666,198 B2 | 2/2010 | Suyker et al. | |
| 7,669,747 B2 | 3/2010 | Weisenburgh, II et al. | |
| 7,717,313 B2 | 5/2010 | Criscuolo et al. | |
| 7,722,642 B2 | 5/2010 | Williamson, IV et al. | |
| 7,744,627 B2 | 6/2010 | Orban, III et al. | |
| 7,776,060 B2 | 8/2010 | Mooradian et al. | |
| 7,780,663 B2* | 8/2010 | Yates | A61B 17/07207 606/151 |
| 7,793,813 B2 | 9/2010 | Bettuchi | |
| 7,799,026 B2 | 9/2010 | Schechter et al. | |
| 7,823,592 B2 | 11/2010 | Bettuchi et al. | |
| 7,824,420 B2 | 11/2010 | Eldridge et al. | |
| 7,845,533 B2 | 12/2010 | Marczyk et al. | |
| 7,845,536 B2 | 12/2010 | Viola et al. | |
| 7,846,149 B2 | 12/2010 | Jankowski | |
| 7,892,247 B2 | 2/2011 | Conston et al. | |
| 7,909,224 B2 | 3/2011 | Prommersberger | |
| 7,909,837 B2 | 3/2011 | Crews et al. | |
| 7,938,307 B2 | 5/2011 | Bettuchi | |
| 7,942,890 B2 | 5/2011 | D'Agostino et al. | |
| 7,950,561 B2 | 5/2011 | Aranyi | |
| 7,951,166 B2 | 5/2011 | Orban, III et al. | |
| 7,951,248 B1 | 5/2011 | Fallis et al. | |
| 7,967,179 B2 | 6/2011 | Olson et al. | |
| 7,988,027 B2 | 8/2011 | Olson et al. | |
| 8,011,550 B2 | 9/2011 | Aranyi et al. | |
| 8,011,555 B2 | 9/2011 | Tarinelli et al. | |
| 8,016,177 B2 | 9/2011 | Bettuchi et al. | |
| 8,016,178 B2 | 9/2011 | Olson et al. | |
| 8,028,883 B2 | 10/2011 | Stopek | |
| 8,033,483 B2 | 10/2011 | Fortier et al. | |
| 8,038,045 B2 | 10/2011 | Bettuchi et al. | |
| 8,062,330 B2 | 11/2011 | Prommersberger et al. | |
| 8,083,119 B2 | 12/2011 | Prommersberger | |
| 8,123,766 B2 | 2/2012 | Bauman et al. | |
| 8,123,767 B2 | 2/2012 | Bauman et al. | |
| 8,146,791 B2 | 4/2012 | Bettuchi et al. | |
| 8,152,777 B2 | 4/2012 | Campbell et al. | |
| 8,157,149 B2 | 4/2012 | Olson et al. | |
| 8,157,151 B2 | 4/2012 | Ingmanson et al. | |
| 8,167,895 B2 | 5/2012 | D'Agostino et al. | |
| 8,192,460 B2 | 6/2012 | Orban, III et al. | |
| 8,210,414 B2 | 7/2012 | Bettuchi et al. | |
| 8,225,799 B2 | 7/2012 | Bettuchi | |
| 8,225,981 B2 | 7/2012 | Criscuolo et al. | |
| 8,231,043 B2 | 7/2012 | Tarinelli et al. | |
| 8,235,273 B2 | 8/2012 | Olson et al. | |
| 8,245,901 B2 | 8/2012 | Stopek | |
| 8,256,654 B2 | 9/2012 | Bettuchi et al. | |
| 8,257,391 B2 | 9/2012 | Orban, III et al. | |
| 8,276,800 B2 | 10/2012 | Bettuchi | |
| 8,286,849 B2 | 10/2012 | Bettuchi | |
| 8,308,042 B2 | 11/2012 | Aranyi | |
| 8,308,045 B2 | 11/2012 | Bettuchi et al. | |
| 8,308,046 B2 | 11/2012 | Prommersberger | |
| 8,312,885 B2 | 11/2012 | Bettuchi et al. | |
| 8,313,014 B2 | 11/2012 | Bettuchi | |
| 8,348,126 B2 | 1/2013 | Olson et al. | |
| 8,348,130 B2 | 1/2013 | Shah et al. | |
| 8,365,972 B2 | 2/2013 | Aranyi et al. | |
| 8,371,491 B2 | 2/2013 | Huitema et al. | |
| 8,371,492 B2 | 2/2013 | Aranyi et al. | |
| 8,371,493 B2 | 2/2013 | Aranyi et al. | |
| 8,393,514 B2 | 3/2013 | Shelton, IV et al. | |
| 8,408,440 B2 | 4/2013 | Olson et al. | |
| 8,413,871 B2 | 4/2013 | Racenet et al. | |
| 8,419,758 B2* | 4/2013 | Smith | A61B 17/1285 606/169 |
| 8,424,742 B2 | 4/2013 | Bettuchi | |
| 8,453,652 B2 | 6/2013 | Stopek | |
| 8,453,904 B2 | 6/2013 | Eskaros et al. | |
| 8,453,909 B2 | 6/2013 | Olson et al. | |
| 8,453,910 B2 | 6/2013 | Bettuchi et al. | |
| 8,464,925 B2 | 6/2013 | Hull et al. | |
| 8,474,677 B2 | 7/2013 | Woodard, Jr. et al. | |
| 8,479,968 B2 | 7/2013 | Hodgkinson et al. | |
| 8,485,414 B2 | 7/2013 | Criscuolo et al. | |
| 8,496,683 B2 | 7/2013 | Prommersberger et al. | |
| 8,511,533 B2 | 8/2013 | Viola et al. | |
| 8,512,402 B2 | 8/2013 | Marczyk et al. | |
| 8,529,600 B2 | 9/2013 | Woodard, Jr. et al. | |
| 8,540,131 B2 | 9/2013 | Swayze | |
| 8,551,138 B2 | 10/2013 | Orban, III et al. | |
| 8,556,918 B2 | 10/2013 | Bauman et al. | |
| 8,561,873 B2 | 10/2013 | Ingmanson et al. | |
| 8,574,252 B2* | 11/2013 | Young | A61B 17/320092 606/169 |
| 8,584,920 B2* | 11/2013 | Hodgkinson | A61B 17/0682 227/175.1 |
| 8,590,762 B2 | 11/2013 | Hess et al. | |
| 8,616,430 B2 | 12/2013 | (Prommersberger) Stopek et al. | |
| 8,631,989 B2 | 1/2014 | Aranyi et al. | |
| 8,668,129 B2 | 3/2014 | Olson | |
| 8,684,250 B2 | 4/2014 | Bettuchi et al. | |
| 8,685,020 B2* | 4/2014 | Weizman | A61B 18/1445 606/207 |
| 8,702,704 B2* | 4/2014 | Shelton, IV | A61B 18/1445 606/51 |
| 8,757,466 B2 | 6/2014 | Olson et al. | |
| 8,789,737 B2 | 7/2014 | Hodgkinson et al. | |
| 8,820,606 B2 | 9/2014 | Hodgkinson | |

(56) References Cited

U.S. PATENT DOCUMENTS

| | | | |
|---|---|---|---|
| 9,192,384 B2* | 11/2015 | Bettuchi | A61B 17/07292 |
| 9,402,687 B2* | 8/2016 | Parihar | A61B 18/1445 |
| 2002/0028243 A1 | 3/2002 | Masters | |
| 2002/0086990 A1 | 7/2002 | Kumar et al. | |
| 2002/0091397 A1 | 7/2002 | Chen | |
| 2002/0165541 A1* | 11/2002 | Whitman | A61B 17/320068 606/48 |
| 2003/0065345 A1 | 4/2003 | Weadock | |
| 2003/0078209 A1 | 4/2003 | Schmidt | |
| 2003/0083676 A1 | 5/2003 | Wallace | |
| 2003/0120284 A1 | 6/2003 | Palacios et al. | |
| 2003/0181927 A1 | 9/2003 | Wallace | |
| 2003/0183671 A1 | 10/2003 | Mooradian et al. | |
| 2003/0208231 A1 | 11/2003 | Williamson et al. | |
| 2004/0107006 A1 | 6/2004 | Francis et al. | |
| 2004/0254590 A1 | 12/2004 | Hoffman et al. | |
| 2004/0260315 A1 | 12/2004 | Dell et al. | |
| 2005/0002981 A1 | 1/2005 | Lahtinen et al. | |
| 2005/0021026 A1* | 1/2005 | Baily | A61B 18/1445 606/51 |
| 2005/0021085 A1 | 1/2005 | Abrams et al. | |
| 2005/0059996 A1 | 3/2005 | Bauman et al. | |
| 2005/0059997 A1 | 3/2005 | Bauman et al. | |
| 2005/0070929 A1 | 3/2005 | Dalessandro et al. | |
| 2005/0118435 A1 | 6/2005 | DeLucia et al. | |
| 2005/0131225 A1 | 6/2005 | Kumar et al. | |
| 2005/0149073 A1 | 7/2005 | Arani et al. | |
| 2005/0154093 A1 | 7/2005 | Kwon et al. | |
| 2006/0004407 A1 | 1/2006 | Hiles et al. | |
| 2006/0008505 A1 | 1/2006 | Brandon | |
| 2006/0093672 A1 | 5/2006 | Kumar et al. | |
| 2006/0121266 A1 | 6/2006 | Fandel et al. | |
| 2006/0135992 A1 | 6/2006 | Bettuchi et al. | |
| 2006/0173470 A1 | 8/2006 | Oray et al. | |
| 2006/0178683 A1 | 8/2006 | Shimoji et al. | |
| 2006/0271104 A1 | 11/2006 | Viola et al. | |
| 2007/0026031 A1 | 2/2007 | Bauman et al. | |
| 2007/0034669 A1 | 2/2007 | de la Torre et al. | |
| 2007/0049953 A2 | 3/2007 | Shimoji et al. | |
| 2007/0054880 A1 | 3/2007 | Saferstein et al. | |
| 2007/0123839 A1 | 5/2007 | Rousseau et al. | |
| 2007/0179528 A1 | 8/2007 | Soltz et al. | |
| 2007/0191713 A1* | 8/2007 | Eichmann | A61B 17/1606 600/471 |
| 2007/0203509 A1 | 8/2007 | Bettuchi | |
| 2007/0203510 A1 | 8/2007 | Bettuchi | |
| 2007/0213522 A1 | 9/2007 | Harris et al. | |
| 2007/0237741 A1 | 10/2007 | Figuly et al. | |
| 2007/0237742 A1 | 10/2007 | Figuly et al. | |
| 2007/0246505 A1 | 10/2007 | Pace-Floridia et al. | |
| 2008/0029570 A1 | 2/2008 | Shelton et al. | |
| 2008/0082126 A1 | 4/2008 | Murray et al. | |
| 2008/0110959 A1 | 5/2008 | Orban et al. | |
| 2008/0125812 A1 | 5/2008 | Zubik et al. | |
| 2008/0140115 A1 | 6/2008 | Stopek | |
| 2008/0161831 A1 | 7/2008 | Bauman et al. | |
| 2008/0161832 A1 | 7/2008 | Bauman et al. | |
| 2008/0164440 A1 | 7/2008 | Maase et al. | |
| 2008/0169327 A1 | 7/2008 | Shelton et al. | |
| 2008/0169328 A1 | 7/2008 | Shelton | |
| 2008/0169329 A1 | 7/2008 | Shelton et al. | |
| 2008/0169330 A1 | 7/2008 | Shelton et al. | |
| 2008/0169331 A1 | 7/2008 | Shelton et al. | |
| 2008/0169332 A1 | 7/2008 | Shelton et al. | |
| 2008/0169333 A1 | 7/2008 | Shelton et al. | |
| 2008/0194805 A1 | 8/2008 | Vignon et al. | |
| 2008/0200940 A1* | 8/2008 | Eichmann | A61B 17/320068 606/169 |
| 2008/0200949 A1 | 8/2008 | Hiles et al. | |
| 2008/0214695 A1 | 9/2008 | Pathak et al. | |
| 2008/0290134 A1 | 11/2008 | Bettuchi et al. | |
| 2008/0308608 A1 | 12/2008 | Prommersberger | |
| 2008/0314960 A1 | 12/2008 | Marczyk et al. | |
| 2009/0001121 A1 | 1/2009 | Hess et al. | |
| 2009/0001122 A1 | 1/2009 | Prommersberger et al. | |
| 2009/0001123 A1 | 1/2009 | Morgan et al. | |
| 2009/0001124 A1 | 1/2009 | Hess et al. | |
| 2009/0001125 A1 | 1/2009 | Hess et al. | |
| 2009/0001126 A1 | 1/2009 | Hess et al. | |
| 2009/0001128 A1 | 1/2009 | Weisenburgh, II et al. | |
| 2009/0001130 A1 | 1/2009 | Hess et al. | |
| 2009/0005808 A1 | 1/2009 | Hess et al. | |
| 2009/0030452 A1 | 1/2009 | Bauman et al. | |
| 2009/0043334 A1 | 2/2009 | Bauman et al. | |
| 2009/0076510 A1 | 3/2009 | Bell et al. | |
| 2009/0076528 A1 | 3/2009 | Sgro | |
| 2009/0078739 A1 | 3/2009 | Viola | |
| 2009/0095791 A1 | 4/2009 | Eskaros et al. | |
| 2009/0095792 A1 | 4/2009 | Bettuchi | |
| 2009/0120994 A1 | 5/2009 | Murray et al. | |
| 2009/0134200 A1 | 5/2009 | Tarinelli et al. | |
| 2009/0206125 A1 | 8/2009 | Huitema et al. | |
| 2009/0206126 A1 | 8/2009 | Huitema et al. | |
| 2009/0206139 A1 | 8/2009 | Hall et al. | |
| 2009/0206141 A1 | 8/2009 | Huitema et al. | |
| 2009/0206142 A1 | 8/2009 | Huitema et al. | |
| 2009/0206143 A1 | 8/2009 | Huitema et al. | |
| 2009/0218384 A1 | 9/2009 | Aranyi | |
| 2009/0220560 A1 | 9/2009 | Wan et al. | |
| 2009/0263441 A1 | 10/2009 | McKay | |
| 2009/0277947 A1 | 11/2009 | Viola | |
| 2009/0287230 A1 | 11/2009 | D'Agostino et al. | |
| 2010/0012704 A1 | 1/2010 | Tarinelli Racenet et al. | |
| 2010/0036405 A1* | 2/2010 | Giordano | A61B 5/0538 606/169 |
| 2010/0065606 A1 | 3/2010 | Stopek | |
| 2010/0065607 A1 | 3/2010 | Orban, III et al. | |
| 2010/0065660 A1 | 3/2010 | Hull et al. | |
| 2010/0072254 A1 | 3/2010 | Aranyi et al. | |
| 2010/0092710 A1 | 4/2010 | Welker et al. | |
| 2010/0096481 A1 | 4/2010 | Hull et al. | |
| 2010/0147921 A1 | 6/2010 | Olson | |
| 2010/0147922 A1* | 6/2010 | Olson | A61B 17/072 227/176.1 |
| 2010/0147923 A1 | 6/2010 | D'Agostino et al. | |
| 2010/0203151 A1 | 8/2010 | Hiraoka | |
| 2010/0243707 A1 | 9/2010 | Olson et al. | |
| 2010/0243708 A1 | 9/2010 | Aranyi et al. | |
| 2010/0243711 A1 | 9/2010 | Olson et al. | |
| 2010/0249805 A1 | 9/2010 | Olson et al. | |
| 2010/0264195 A1 | 10/2010 | Bettuchi | |
| 2010/0282815 A1 | 11/2010 | Bettuchi et al. | |
| 2011/0024476 A1 | 2/2011 | Bettuchi et al. | |
| 2011/0024481 A1 | 2/2011 | Bettuchi et al. | |
| 2011/0036894 A1 | 2/2011 | Bettuchi | |
| 2011/0042442 A1 | 2/2011 | Viola et al. | |
| 2011/0046650 A1 | 2/2011 | Bettuchi | |
| 2011/0057016 A1 | 3/2011 | Bettuchi | |
| 2011/0082427 A1 | 4/2011 | Golzarian et al. | |
| 2011/0087279 A1 | 4/2011 | Shah et al. | |
| 2011/0089375 A1 | 4/2011 | Chan et al. | |
| 2011/0215132 A1 | 9/2011 | Aranyi et al. | |
| 2011/0293690 A1 | 12/2011 | Griffin et al. | |
| 2012/0071866 A1* | 3/2012 | Kerr | A61B 17/07207 606/13 |
| 2012/0074199 A1 | 3/2012 | Olson et al. | |
| 2012/0080336 A1 | 4/2012 | Shelton, IV et al. | |
| 2012/0089131 A1 | 4/2012 | Zemlok et al. | |
| 2012/0150176 A1* | 6/2012 | Weizman | A61B 17/07207 606/45 |
| 2012/0156289 A1 | 6/2012 | Blaskovich et al. | |
| 2012/0184946 A1* | 7/2012 | Price | A61B 17/320092 606/1 |
| 2012/0187179 A1 | 7/2012 | Gleiman | |
| 2012/0241499 A1 | 9/2012 | Baxter, III et al. | |
| 2012/0253329 A1 | 10/2012 | Zemlok et al. | |
| 2012/0273547 A1 | 11/2012 | Hodgkinson et al. | |
| 2013/0023868 A1* | 1/2013 | Worrell | A61B 17/07207 606/33 |
| 2013/0037596 A1 | 2/2013 | Bear et al. | |
| 2013/0105548 A1 | 5/2013 | Hodgkinson et al. | |
| 2013/0105553 A1 | 5/2013 | (Tarinelli) Racenet et al. | |
| 2013/0112732 A1 | 5/2013 | Aranyi et al. | |
| 2013/0112733 A1 | 5/2013 | Aranyi et al. | |

(56) References Cited

U.S. PATENT DOCUMENTS

| | | | |
|---|---|---|---|
| 2013/0146641 A1 | 6/2013 | Shelton, IV et al. | |
| 2013/0146642 A1 | 6/2013 | Shelton, IV et al. | |
| 2013/0153633 A1 | 6/2013 | Casasanta, Jr. et al. | |
| 2013/0153634 A1 | 6/2013 | Carter et al. | |
| 2013/0153635 A1 | 6/2013 | Hodgkinson | |
| 2013/0153636 A1 | 6/2013 | Shelton, IV et al. | |
| 2013/0153638 A1 | 6/2013 | Carter et al. | |
| 2013/0153639 A1 | 6/2013 | Hodgkinson et al. | |
| 2013/0153640 A1* | 6/2013 | Hodgkinson | A61B 17/07207 227/180.1 |
| 2013/0153641 A1 | 6/2013 | Shelton, IV et al. | |
| 2013/0161374 A1 | 6/2013 | Swayze et al. | |
| 2013/0181031 A1 | 7/2013 | Olson et al. | |
| 2013/0193186 A1 | 8/2013 | (Tarinelli) Racenet et al. | |
| 2013/0193190 A1 | 8/2013 | Carter et al. | |
| 2013/0193191 A1 | 8/2013 | Stevenson et al. | |
| 2013/0193192 A1 | 8/2013 | Casasanta, Jr. et al. | |
| 2013/0209659 A1 | 8/2013 | Racenet et al. | |
| 2013/0221062 A1 | 8/2013 | Hodgkinson | |
| 2013/0240600 A1 | 9/2013 | Bettuchi | |
| 2013/0240601 A1 | 9/2013 | Bettuchi et al. | |
| 2013/0240602 A1 | 9/2013 | Stopek | |
| 2013/0277411 A1 | 10/2013 | Hodgkinson et al. | |
| 2013/0306707 A1 | 11/2013 | Viola et al. | |
| 2013/0310873 A1 | 11/2013 | Stopek (nee Prommersberger) et al. | |
| 2013/0327807 A1 | 12/2013 | Olson et al. | |
| 2014/0012317 A1 | 1/2014 | Orban et al. | |
| 2014/0021242 A1 | 1/2014 | Hodgkinson et al. | |
| 2014/0027490 A1 | 1/2014 | Marczyk et al. | |
| 2014/0034704 A1 | 2/2014 | Ingmanson et al. | |
| 2014/0048580 A1 | 2/2014 | Merchant et al. | |
| 2014/0061280 A1 | 3/2014 | Ingmanson et al. | |
| 2014/0061281 A1 | 3/2014 | Hodgkinson | |
| 2014/0084042 A1 | 3/2014 | (Prommersberger) Stopek et al. | |
| 2014/0097224 A1 | 4/2014 | Prior | |
| 2014/0117066 A1 | 5/2014 | Aranyi et al. | |
| 2014/0130330 A1 | 5/2014 | Olson et al. | |
| 2014/0131418 A1 | 5/2014 | Kostrzewski | |
| 2014/0131419 A1 | 5/2014 | Bettuchi | |
| 2014/0138423 A1 | 5/2014 | Whitfield et al. | |
| 2014/0151428 A1* | 6/2014 | Boudreaux | A61B 18/1445 227/175.1 |
| 2014/0151431 A1 | 6/2014 | Hodgkinson et al. | |
| 2014/0155916 A1 | 6/2014 | Hodgkinson et al. | |
| 2014/0158742 A1 | 6/2014 | Stopek (nee Prommersberger) et al. | |
| 2014/0166721 A1* | 6/2014 | Stevenson | A61B 17/068 227/176.1 |
| 2014/0197224 A1 | 7/2014 | Penna | |
| 2014/0203061 A1 | 7/2014 | Hodgkinson | |
| 2014/0207124 A1* | 7/2014 | Aldridge | A61B 17/00234 606/1 |
| 2014/0217147 A1 | 8/2014 | Milliman | |
| 2014/0217148 A1 | 8/2014 | Penna | |
| 2014/0239046 A1 | 8/2014 | Milliman | |
| 2014/0239047 A1 | 8/2014 | Hodgkinson et al. | |
| 2014/0276723 A1* | 9/2014 | Parihar | A61B 17/07207 606/33 |
| 2015/0011988 A1 | 1/2015 | Whitman | |
| 2015/0048142 A1* | 2/2015 | Scheib | A61B 17/064 227/180.1 |
| 2015/0048143 A1* | 2/2015 | Scheib | A61B 17/0643 227/180.1 |
| 2017/0042605 A1* | 2/2017 | Worrell | A61B 17/07207 |
| 2017/0172575 A1* | 6/2017 | Hodgkinson | A61B 17/07207 |

FOREIGN PATENT DOCUMENTS

| | | | |
|---|---|---|---|
| EP | 0 327 022 A2 | 8/1989 | |
| EP | 0 594 148 A1 | 4/1994 | |
| EP | 0 667 119 A1 | 8/1995 | |
| EP | 0695535 A1 | 2/1996 | |
| EP | 1 064 883 A1 | 1/2001 | |
| EP | 1 256 317 A2 | 11/2002 | |
| EP | 1 256 318 A1 | 11/2002 | |
| EP | 1 520 525 A1 | 4/2005 | |
| EP | 1 621 141 A2 | 2/2006 | |
| EP | 1 702 570 A1 | 9/2006 | |
| EP | 1 759 640 A2 | 3/2007 | |
| EP | 1 815 804 A2 | 8/2007 | |
| EP | 1 825 820 A1 | 8/2007 | |
| EP | 1 929 958 A2 | 6/2008 | |
| EP | 1 994 890 A1 | 11/2008 | |
| EP | 2 005 894 A2 | 12/2008 | |
| EP | 2 005 895 A2 | 12/2008 | |
| EP | 2 008 595 A2 | 12/2008 | |
| EP | 2 090 231 A1 | 8/2009 | |
| EP | 2 090 244 A2 | 8/2009 | |
| EP | 2 090 252 A2 | 8/2009 | |
| EP | 2 198 787 A1 | 6/2010 | |
| EP | 2 236 098 A2 | 10/2010 | |
| EP | 2 236 099 A1 | 10/2010 | |
| EP | 2 311 386 A2 | 4/2011 | |
| EP | 2 436 348 A1 | 4/2012 | |
| EP | 2 462 880 A2 | 6/2012 | |
| EP | 2 517 637 A1 | 10/2012 | |
| EP | 2 586 380 A1 | 5/2013 | |
| EP | 2 604 195 A1 | 6/2013 | |
| EP | 2 604 197 A2 | 6/2013 | |
| EP | 2 620 106 A2 | 7/2013 | |
| EP | 2 630 922 A1 | 8/2013 | |
| EP | 2 644 125 A2 | 10/2013 | |
| JP | 2000-166933 A | 6/2000 | |
| JP | 2002-202213 A | 7/2002 | |
| JP | 2007-124166 A | 5/2007 | |
| WO | 90/05489 A1 | 5/1990 | |
| WO | 95/16221 A1 | 6/1995 | |
| WO | 96/22055 A1 | 7/1996 | |
| WO | 97/01989 A1 | 1/1997 | |
| WO | 97/13463 A1 | 4/1997 | |
| WO | 98/17180 A1 | 4/1998 | |
| WO | 99/45849 A1 | 9/1999 | |
| WO | 03/088845 A2 | 10/2003 | |
| WO | 03082126 A1 | 10/2003 | |
| WO | 03/094743 A1 | 11/2003 | |
| WO | 03/105698 A2 | 12/2003 | |
| WO | 2005079675 A2 | 9/2005 | |
| WO | 2006023578 A2 | 3/2006 | |
| WO | 2006044490 A2 | 4/2006 | |
| WO | 2006083748 A1 | 8/2006 | |
| WO | 2007121579 A1 | 11/2007 | |
| WO | 2008057281 A2 | 5/2008 | |
| WO | 2008109125 A1 | 9/2008 | |
| WO | 2010075298 A2 | 7/2010 | |
| WO | 2011143183 A2 | 11/2011 | |
| WO | 2012044848 A1 | 4/2012 | |
| WO | 2013/119463 A1 | 8/2013 | |
| WO | WO 2013119463 A1 * | 8/2013 | A61B 18/04 |

OTHER PUBLICATIONS

Extended European Search Report corresponding to EP 14 15 7195.0, completed Jun. 5, 2014 and dated Jun. 18, 2014; (9 pp).

Extended European Search Report corresponding to EP 14 15 6342.9, completed Jul. 22, 2014 and dated Jul. 29, 2014; (8 pp).

Extended European Search Report for EP 16 15 4792 dated Aug. 31, 2016.

European Search Report corresponding to EP 05 02 2585.3, completed Jan. 25, 2006 and dated Feb. 3, 2006; (4 pp).

European Search Report corresponding to EP 06 00 4598, completed Jun. 22, 2006; (2 pp).

European Search Report corresponding to EP 06 01 6962.0, completed Jan. 3, 2007 and dated Jan. 11, 2007; (10 pp).

International Search Report corresponding to International Application No. PCT/US2005/036740, completed Feb. 20, 2007 and dated Mar. 23, 2007; (8 pp).

International Search Report corresponding to International Application No. PCT/US2007/022713, completed Apr. 21, 2008 and dated May 15, 2008; (1 p).

(56) References Cited

OTHER PUBLICATIONS

International Search Report corresponding to International Application No. PCT/US2008/002981, completed Jun. 9, 2008 and dated Jun. 26, 2008; (2 pp).
European Search Report corresponding to EP 08 25 1779, completed Jul. 14, 2008 and dated Jul. 23, 2008; (5 pp).
European Search Report corresponding to EP 08 25 1989.3, completed Mar. 11, 2010 and dated Mar. 24, 2010; (6 pp).
European Search Report corresponding to EP 10 25 0639.1, completed Jun. 17, 2010 and dated Jun. 28, 2010; (7 pp).
European Search Report corresponding to EP 10 25 0715.9, completed Jun. 30, 2010 and dated Jul. 20, 2010; (3 pp).
European Search Report corresponding to EP 05 80 4382.9, completed Oct. 5, 2010 and dated Oct. 12, 2010; (3 pp).
European Search Report corresponding to EP 10 25 1437.9, completed Nov. 22, 2010 and dated Dec. 16, 2010; (3 pp).
European Search Report corresponding to EP 09 25 2897.5, completed Feb. 7, 2011 and dated Feb. 15, 2011; (3 pp).
European Search Report corresponding to EP 10 25 0642.5, completed Mar. 25, 2011 and dated Apr. 4, 2011; (4 pp).
European Search Report corresponding to EP 11 18 8309.6, completed Dec. 15, 2011 and dated Jan. 12, 2012; (3 pp).
European Search Report corresponding to EP 12 15 2229.6, completed Feb. 23, 2012 and dated Mar. 1, 2012; (4 pp).
European Search Report corresponding to EP 12 15 0511.9, completed Apr. 16, 2012 and dated Apr. 24, 2012; (7 pp).
European Search Report corresponding to EP 12 15 2541.4, completed Apr. 23, 2012 and dated May 3, 2012; (10 pp).
European Search Report corresponding to EP 12 16 5609.4, completed Jul. 5, 2012 and dated Jul. 13, 2012; (8 pp).
European Search Report corresponding to EP 12 15 8861.0, completed Jul. 17, 2012 and dated Jul. 24, 2012; (9 pp).
European Search Report corresponding to EP 12 16 5878.5, completed Jul. 24, 2012 and dated Aug. 6, 2012; (8 pp).
Extended European Search Report corresponding to EP 12 19 1035.0, completed Jan. 11, 2013 and dated Jan. 18, 2013; (7 pp).
Extended European Search Report corresponding to EP 12 18 6175.1, completed Jan. 15, 2013 and dated Jan. 23, 2013; (7 pp).
Extended European Search Report corresponding to EP 12 19 1114.3, completed Jan. 23, 2013 and dated Jan. 31, 2013; (10 pp).
Extended European Search Report corresponding to EP 12 19 2224.9, completed Mar. 14, 2013 and dated Mar. 26, 2013; (8 pp).
Extended European Search Report corresponding to EP 12 19 6904.2, completed Mar. 28, 2013 and dated Jul. 26, 2013; (8 pp).
Extended European Search Report corresponding to EP 12 19 6911.7, completed Apr. 18, 2013 and dated Apr. 24, 2013; (8 pp).
Extended European Search Report corresponding to EP 07 00 5842.5, completed May 13, 2013 and dated May 29, 2013; (7 pp).
Extended European Search Report corresponding to EP 12 19 8776.2, completed May 16, 2013 and dated May 27, 2013; (8 pp).
Extended European Search Report corresponding to EP 12 19 8749.9, completed May 21, 2013 and dated May 31, 2013; (8 pp).
Extended European Search Report corresponding to EP 13 15 6297.7, completed Jun. 4, 2013 and dated Jun. 13, 2013I; (7 pp).
Extended European Search Report corresponding to EP 13 17 3985.6, completed Aug. 19, 2013 and dated Aug. 28, 2013; (6 pp).
Extended European Search Report corresponding to EP 13 17 3986.4, completed Aug. 20, 2013 and dated Aug. 29, 2013; (6 pp).
Extended European Search Report corresponding to EP 13 17 7437.4, completed Sep. 11, 2013 and dated Sep. 19, 2013; 6 pages.
Extended European Search Report corresponding to EP 13 17 7441.6, completed Sep. 11, 2013 and dated Sep. 19, 2013; (6 pp).
Extended European Search Report corresponding to EP 07 86 1534.1, completed Sep. 20, 2013 and dated Sep. 30, 2013; (5 pp).
Extended European Search Report corresponding to EP 13 18 3876.5, completed Oct. 14, 2013 and dated Oct. 24, 2013; (5 pp).
Extended European Search Report corresponding to EP 13 17 1856.1, completed Oct. 29, 2013 and dated Nov. 7, 2013; (8 pp).
Extended European Search Report corresponding to EP 13 18 0373.6, completed Oct. 31, 2013 and dated Nov. 13, 2013; (7 pp).
Extended European Search Report corresponding to EP 13 18 0881.8, completed Nov. 5, 2013 and dated Nov. 14, 2013; (6 pp).
Extended European Search Report corresponding to EP 13 17 6895.4, completed Nov. 29, 2013 and dated Dec. 12, 2013; (5 pp).
Extended European Search Report corresponding to EP 13 18 2911.1, completed Dec. 2, 2013 and dated Dec. 16, 2013; (8 pp).
Extended European Search Report corresponding to EP 10 25 1795.0, completed Dec. 11, 2013 and dated Dec. 20, 2013; (6 pp).
Extended European Search Report corresponding to EP 13 18 7911.6, completed Jan. 22, 2014 and dated Jan. 31, 2014; (8 pp).
Extended European Search Report corresponding to EP 13 19 2111.6, completed Feb. 13, 2014 and dated Feb. 27, 2014; (10 pp).
Extended European Search Report corresponding to EP 13 19 5919.9, completed Feb. 10, 2014 and dated Mar. 3, 2014; (7 pp).
Extended European Search Report corresponding to EP 08 72 6500.5, completed Feb. 20, 2014 and dated Mar. 3, 2014; (7 pp).
Extended European Search Report corresponding to EP 13 19 5019.8, completed Mar. 14, 2014 and dated Mar. 24, 2014; (7 pp).
Extended European Search Report corresponding to EP 13 19 6816.6, completed Mar. 28, 2014 and dated Apr. 9, 2014; (9 pp).
Extended European Search Report corresponding to EP 13 19 7958.5, completed Apr. 4, 2014 and dated Apr. 15, 2014; (8 pp).
Australian Examination Report issued in AU Application No. 2016200148, dated Sep. 12, 2019.

* cited by examiner

SURGICAL STAPLING INSTRUMENT HAVING ULTRASONIC ENERGY DELIVERY

BACKGROUND

1. Technical Field

The present disclosure relates generally to surgical stapling instruments. More specifically, the present disclosure relates to stapling instruments including ultrasonic energy delivery.

2. Background of Related Art

Surgical stapling instruments configured to join tissue portions during a surgical procedure are well known. These stapling instruments include linear end effectors which are oriented parallel or transverse to a longitudinal axis of the instrument. These stapling instruments also include circular end effectors.

Stapling instruments can include a knife that cuts tissue between staple lines. Alternatively, some stapling instruments include ultrasonic blades that cut tissue between the staple lines.

Surgical buttress material may be used in combination with stapling instruments to reinforce the staple lines to promote proper staple formation, reduce bleeding, and promote anastomosis of tissue.

SUMMARY

In an aspect of the present disclosure, an end effector includes first and second jaws, first and second buttresses, and an ultrasonic blade. The first jaw includes a fastener cartridge that has a first tissue contacting surface and a plurality of fasteners arranged in rows parallel to a longitudinal axis of the first jaw. The second jaw includes a section tissue contacting surface. The first and second jaws are moveable relative to one another and are configured to grasp tissue therebetween. The first buttress is attached to the first tissue contacting surface. The second buttress is attached to the second tissue contacting surface. The ultrasonic blade is activatable to weld the first buttress to the second buttress and to subsequently cut the welded first and second buttresses and tissue grasped between the first and second jaws.

In aspects, the ultrasonic blade has a first portion that is disposed on the first tissue contacting surface between two rows of the plurality of fasteners. The ultrasonic blade may have a second portion that is disposed on the second tissue contacting surface opposing the first portion of the ultrasonic blade. The second portion may be parallel to a longitudinal axis of the second jaw.

In some aspects, the plurality of fasteners are ejectable from the fastener cartridge and are configured to secure the first and second buttresses about tissue grasped between the first and second jaws. The plurality of fasteners may be staples and the second jaw may include an anvil for deforming the staples as the staples are ejected from the fastener cartridge.

In another aspect of the present disclosure, an end effector includes a first jaw, a second jaw, and an ultrasonic blade. The first jaw includes a fastener cartridge that has a first tissue contacting surface and a plurality of fasteners that are arranged in rows parallel to a longitudinal axis of the first jaw. The fastener cartridge defines a blade channel along its longitudinal axis. The second jaw includes a second tissue contacting surface and a protrusion that opposes the blade channel. The first and second jaws are moveable relative to one another and are configured to grasp tissue therebetween. The ultrasonic blade has first and second portions that are disposed within the blade channel. The first and second portions are each adjacent one of the opposing walls defining the blade channel. The first and second portions define a gap therebetween along the longitudinal axis of the first jaw. The protrusion is disposed within the gap when the first and second jaws are in an approximated configuration.

In aspects, the end effector includes a first buttress attached to the first tissue contacting surface and a second buttress attached to the second tissue contacting surface. The plurality of fasteners may be staples and the second jaw may include an anvil for deforming the staples as the staples are ejected from the fasteners cartridge.

In yet another aspect of the present disclosure, a method of dissecting tissue includes clamping tissue between opposing jaws of an end effector, ejecting fasteners from one of the opposing jaws, and activating an ultrasonic blade. Each of the opposing jaws may include a buttress attached to a tissue contacting surface. Ejecting the fasteners from one of the opposing jaws includes ejecting the fasteners through each of the buttresses to fasten the clamped tissue together. The fasteners are disposed in rows parallel to a longitudinal axis of the end effector. The ultrasonic blade is disposed in a blade channel disposed along the longitudinal axis of the end effector. Activating the ultrasonic blade cuts the tissue and welds the buttresses together. Clamping tissue between the opposing jaws of the end effector may include a protrusion on one jaw urging a portion of the tissue into the blade channel of the opposing jaw.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION OF EMBODIMENTS

Figure 1A:
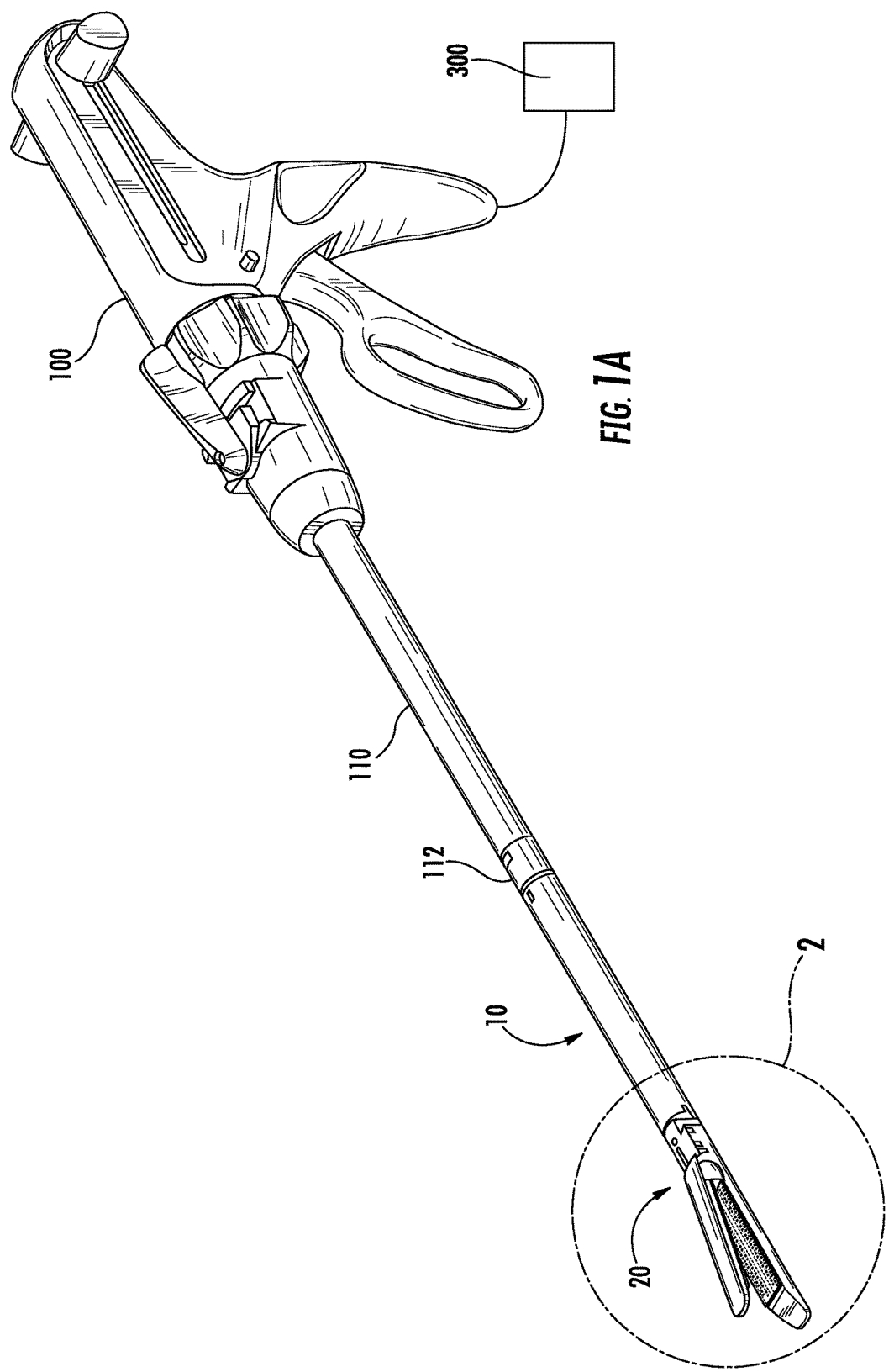
FIG. 1A is a perspective view of a manually actuated handle assembly and a loading unit in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

Figure 1B:
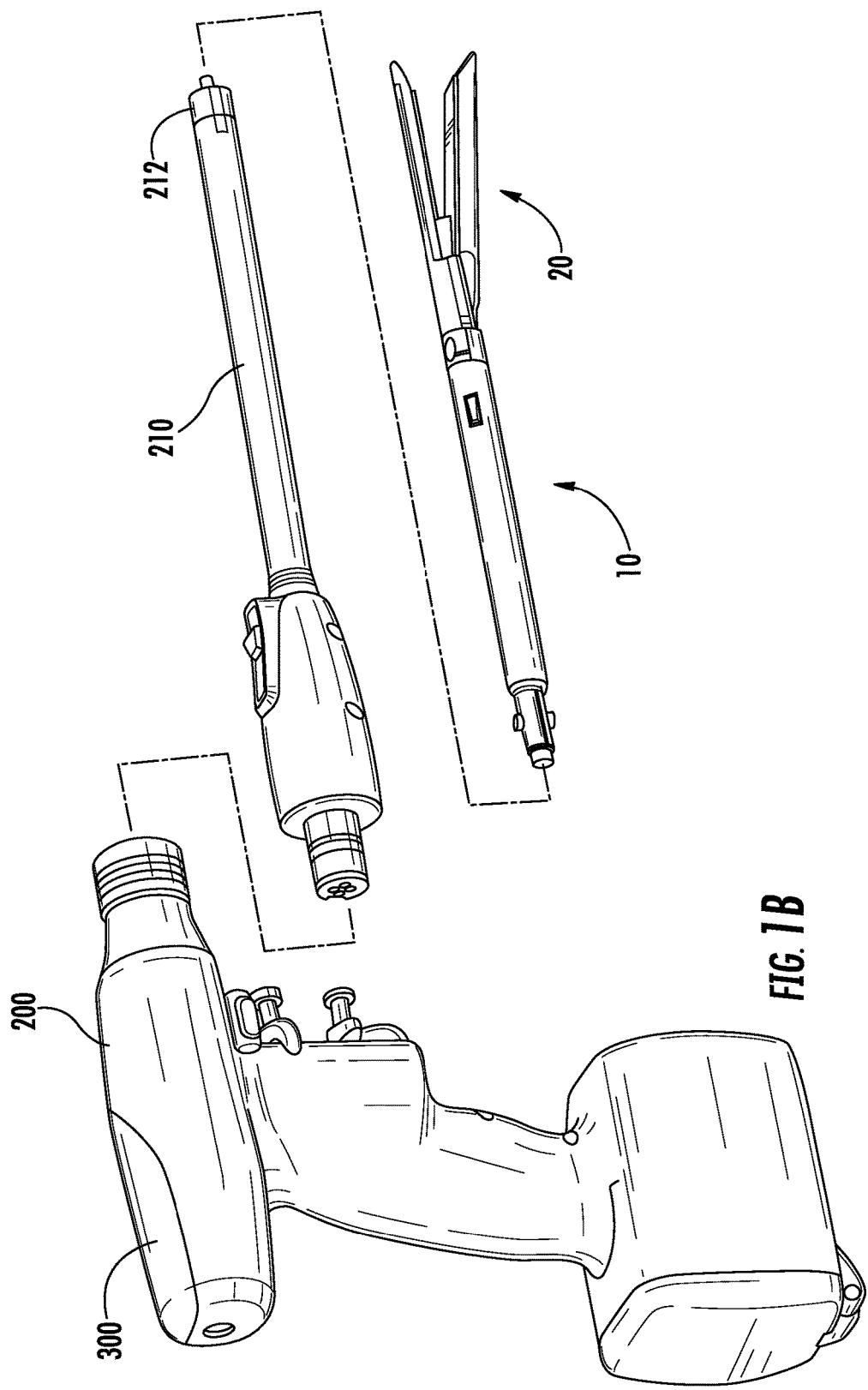
FIG. 1B is a perspective view of an electromechanical instrument, an adaptor, and the loading unit of FIG. 1A.

FIGS. 1A and 1B illustrate a loading unit 10 having an end effector 20 in accordance with an embodiment of the present disclosure. The loading unit 10 is configured for connection to a manually actuated handle assembly or stapling instrument 100 such as described in U.S. Pat. No. 8,789,737 ("the '737 patent"), which is incorporated herein by reference. Alternatively, the loading unit 10 can be configured for selective connection to a powered hand held electromechanical instrument 200 via the adaptor 210. In such an embodiment, the adaptor 210 of the electromechanical instrument 200 may have a configuration similar to that of the elongated body portion 110 of the stapling instrument 100 as shown in FIG. 1A. The loading unit 10 is releasably coupled to a distal end 112 of the elongated body portion 110 of the manually actuated handle assembly 100 or to a distal end 212 of the adaptor 210 of the electromechanical instrument 200. The end effector 20 is operatively associated with an ultrasonic generator 300. As shown in FIG. 1A, the ultrasonic generator 300 may be external to the stapling instrument (e.g., stapling instrument 100 or electromechanical instrument 200). Alternatively, as shown in FIG. 1B, the ultrasonic generator 300 may be incorporated into the stapling instrument (e.g., stapling instrument 100 or electromechanical instrument 200).

For a detailed description of the structure and function of an exemplary adaptor and loading unit, please refer to commonly owned U.S. Patent Publication No. 2012/0089131. For a detailed description of the structure and function of an exemplary electromechanical instrument, please refer to commonly owned U.S. Patent Publication Nos. 2012/0253329 and 2012/0323226. For a detailed description of the structure and function of an exemplary ultrasonic generator, please refer to commonly owned U.S. Pat. No. 8,419,758. Each of these disclosures is incorporated herein by reference in its entirety.

Figure 2:
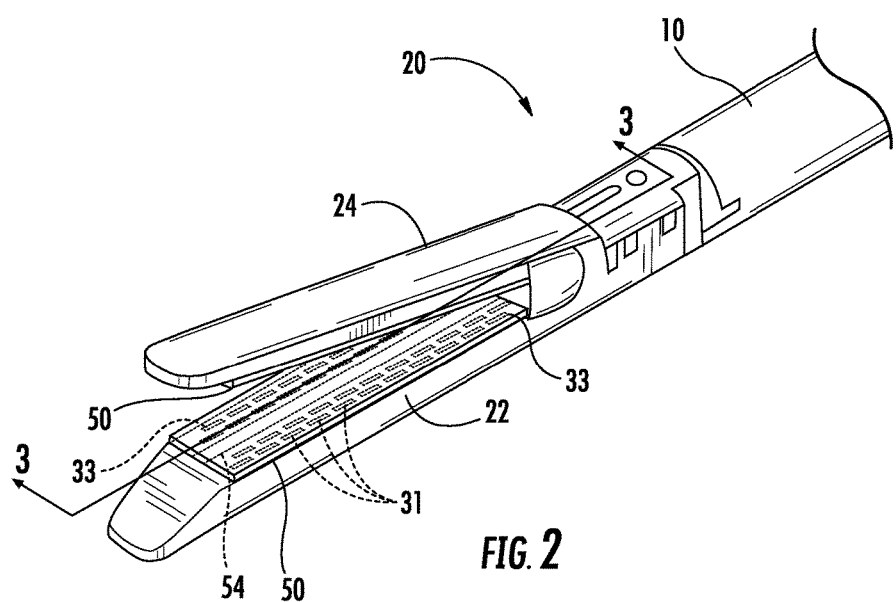
FIG. 2 is an enlarged view of the indicated area of detail of FIG. 1A.
Figure 3:
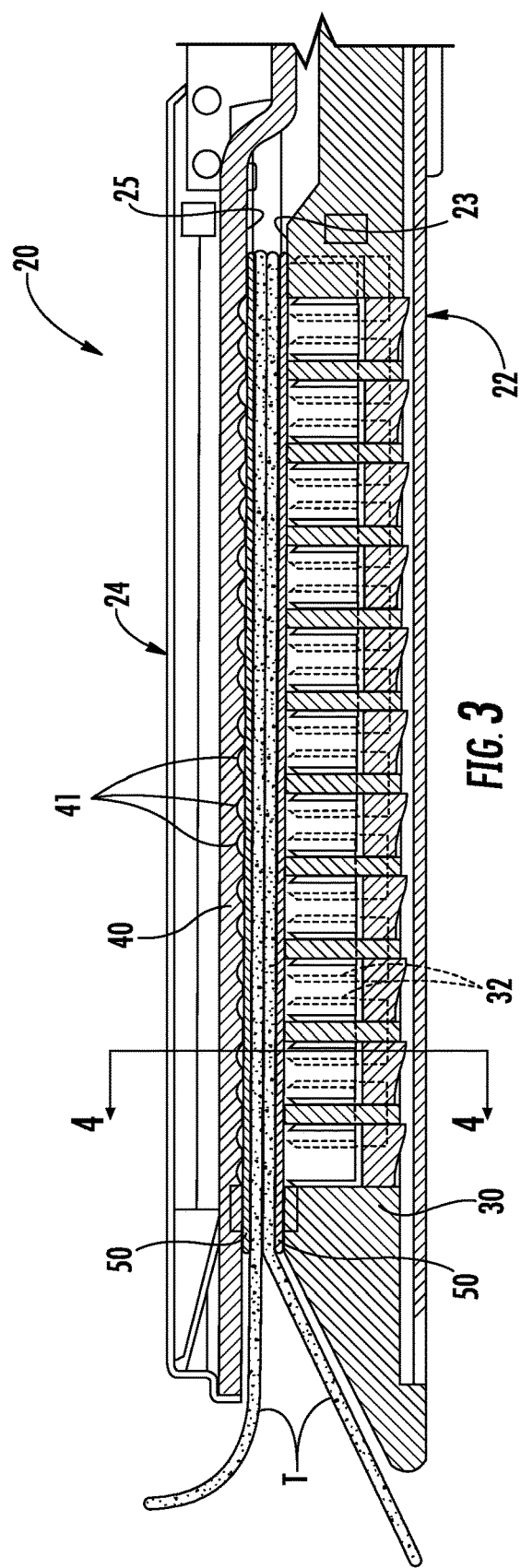
FIG. 3 is a cross-sectional view taken along the section line 3-3 with jaws approximated of FIG. 2.
Figure 4:
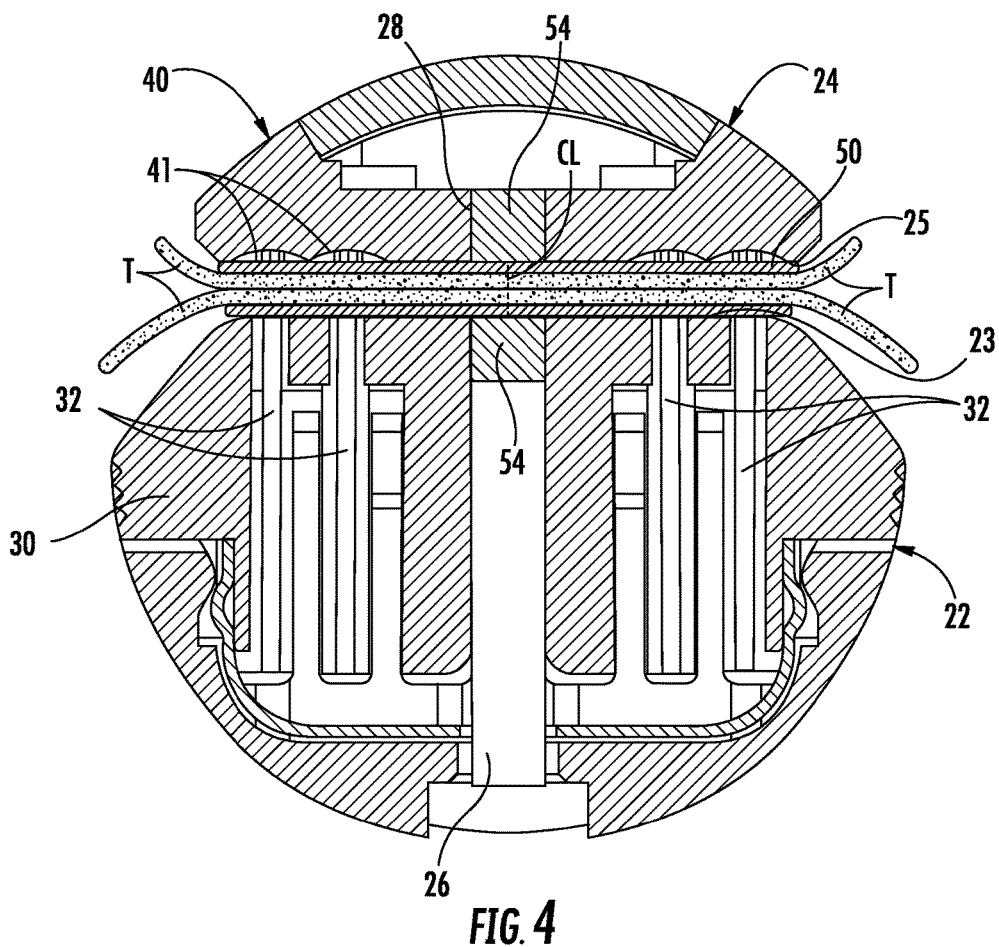
FIG. 4 is a cross-sectional view taken along the section line 4-4 of FIG. 3.

Referring to FIGS. 2 and 3, the loading unit 10 includes a first or lower jaw 22 and a second or upper jaw 24. The upper and lower jaws 22, 24 are moveable relative to one another between a spaced-apart configuration (FIG. 2) and an approximated configuration (FIG. 3). The lower jaw 22 includes a fastener cartridge 30 having a plurality of staples 32 arranged in rows 33 on either side of a knife or lower blade channel 26 (FIG. 4). The fastener cartridge 30 may be releasably coupled to the lower jaw 22. The upper jaw 24 includes an anvil 40 that is configured to deform the staples 32 into formed staples as the staples 32 are ejected through openings 31 of the fastener cartridge 30 when the jaws 22, 24 are in the approximated configuration as detailed below.

Alternatively, the fastener cartridge 30 of the lower jaw 22 may include a plurality of fasteners (not explicitly shown) and the upper jaw 24 may include a retainer cartridge (not shown) that includes a plurality of retainers (not shown). As the fasteners are ejected from the fastener cartridge 30 of the first jaw 22, each of the fasteners forms a two-part fastener with one of the retainers of the retainer cartridge.

With additional reference to FIG. 4, the fastener cartridge 30 and the anvil 40 each include a tissue contacting surface 23, 25, respectively. The end effector 20 may include a buttress 50 releasably disposed on each of the tissue contacting surfaces 23, 25. The buttress 50 may be fabricated from a suitable biocompatible and bioabsorbable material. The buttress 50 may be fabricated from a non-absorbent material which does not retain fluid, or the buttress can be made from an absorbent material. For a detailed description of suitable materials for surgical buttresses, please refer to commonly owned U.S. Pat. Nos. 5,542,594; 5,908,427; 5,964,774; 6,045,560; 7,823,592; and 7,938,307, and commonly assigned U.S. Patent Publication No. 2010/0092710, the entire contents of each of which is incorporated herein by reference. As detailed below, the buttress 50 detaches from the tissue contacting surfaces 23, 25 of the fastener cartridge 30 and the anvil 40 when the staples 32 are ejected from the fastener cartridge 30. As discussed in greater detail below, the buttresses 50 may promote anastomosis, reduce bleeding, provide support for the tissue to facilitate a higher burst pressure, and distribute pressure from the fasteners to a larger area of tissue.

The anvil 40 defines an upper blade channel 28 that opposes the lower blade channel 26 of the fastener cartridge 30. An ultrasonic blade 54 is disposed in each of the blade channels 26, 28. The ultrasonic blades 54 are operatively associated with an ultrasonic generator 300 (FIG. 1A). The ultrasonic generator 300 provides ultrasonic energy to the ultrasonic blades 54 to ultrasonically translate the ultrasonic blades 54 within the blade channels 26, 28. As detailed below, the ultrasonic blades 54 are configured to cut tissue between the jaws 22, 24 along a cut line CL (FIG. 4) in the approximated configuration and to weld the buttress 50 attached to the tissue contacting surface 23 of the lower jaw 22 to buttress 50 attached to the tissue contacting surface 25 of the upper jaw 24.

Figure 5:
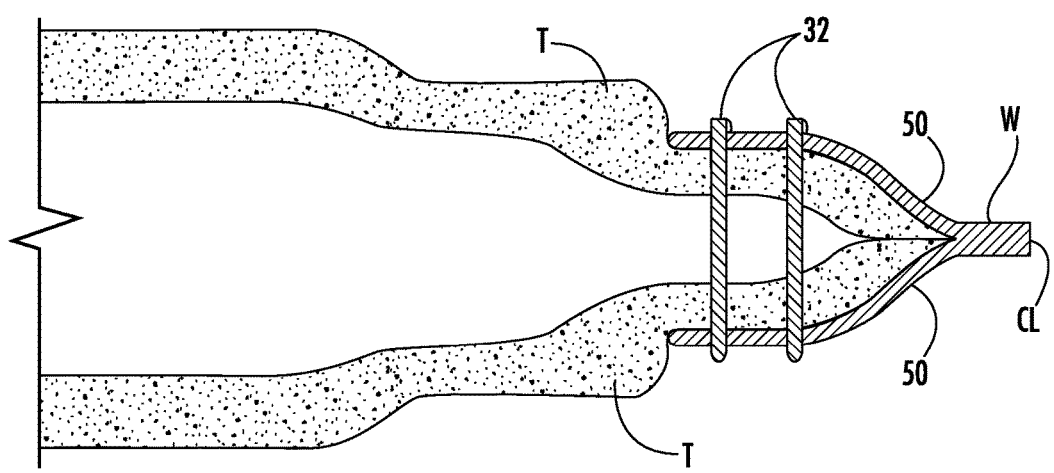
FIG. 5 is a side cross-sectional view of tissue joined with the end effector of FIG. 2.

Referring to FIGS. 4 and 5, the end effector 20 is used to fasten and divide tissue T in accordance with the present disclosure. The jaws 22, 24 of the end effector 20 are approximated over tissue T to be fastened and divided. With layers of the tissue T positioned between the jaws 22, 24, the staples 32 are ejected from the fastener cartridge 30 of the lower jaw 22 towards the anvil 40 of the upper jaw 24. The staples 32 pass through the buttresses 50 and are formed in staple pockets 41 defined by the anvil 40 such that the staples 32 are disposed on either side of the tissue to urge the buttresses 50 towards one another. The staple pockets 41 deform legs of the staples 32 towards one another such that the staples 32 fasten the layers of tissue T to one another. The buttresses 50 compress the layers of tissue T therebetween to promote anastomosis of the tissue T. The ultrasonic blades 54 are then supplied with ultrasonic energy to cut the layers of tissue T between the ultrasonic blades 54 along the cut line CL. As the ultrasonic blades 54 cut the tissue T between the ultrasonic blades 54, the ultrasonic blades 54 weld the buttresses 50 together adjacent the central cut line CL. The weld W (FIG. 5) of the buttresses 50 helps seal the cut portion of the tissue T.

By welding the buttresses 50 together adjacent the cut line CL of the tissue T, bleeding of the tissue T may be reduced when compared to anastomosis from stapling alone. Further, by stapling through the buttresses 50 adjacent the cut line CL, the ultrasonic blades 54 may be used to cut and seal tissue T having a greater thickness when compared to an ultrasonic dissector alone.

Figure 6:
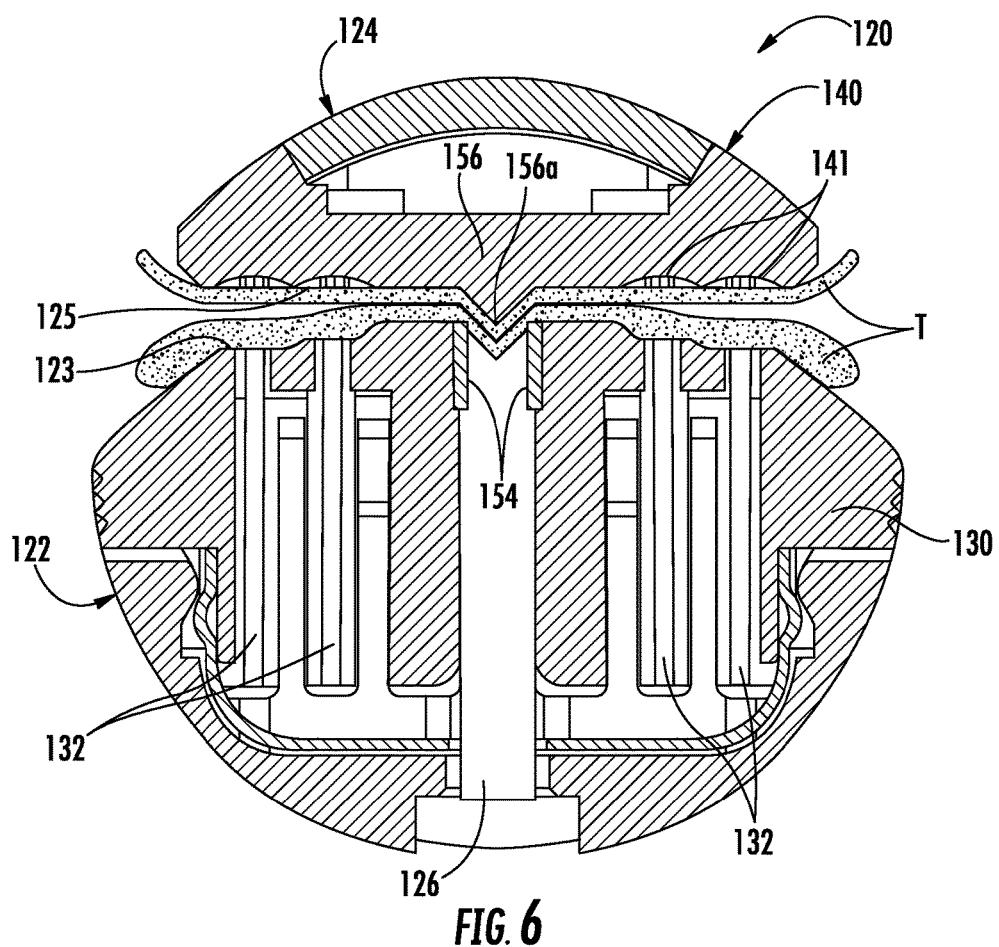
FIG. 6 is a cross-sectional view similar to FIG. 4 of another end effector provided in accordance with the present disclosure.

Referring now to FIG. 6, another end effector 120 is provided in accordance with the present disclosure. The end effector 120 is similar to the end effector 20 detailed above with like structures represented with similar labels, as such only the differences will be discussed in detail below. A lower jaw 122 includes a fastener cartridge 130 and has a stepped tissue contacting surface 123. It is within the scope of this disclosure, that the tissue contacting surface 125 of the anvil 140 may also have a stepped configuration similar to the stepped configuration of the tissue contacting surface 123 of the fastener cartridge 130. The stepped configuration of the tissue contacting surfaces 123, 125 compress tissue T between the jaws 122, 124 in a step like manner which may allow tissue having a greater thickness to be stapled and cut. The fastener cartridge 130 defines a blade channel 126 between rows of fasteners 132. Two ultrasonic blades 154 are disposed within the blade channel 126 adjacent walls defining the blade channel 126.

Referring now to FIG. 6, another end effector 120 is provided in accordance with the present disclosure. The end effector 120 is similar to the end effector 20 detailed above with like structures represented with similar labels, as such only the differences will be discussed in detail below. A lower jaw 122 includes a fastener cartridge 130 and has a stepped tissue contacting surface 123. It is within the scope of this disclosure, that the tissue contacting surface 125 of the anvil 140 may also have a stepped configuration similar to the stepped configuration of the tissue contacting surface 123 of the fastener cartridge 130. The stepped configuration of the tissue contacting surfaces 123, 125 compress tissue T between the jaws 122, 124 in a step like manner which may allow tissue having a greater thickness to be stapled and cut. The fastener cartridge 130 defines a blade channel 126 between rows of fasteners 132. Two ultrasonic blades 154 are disposed within the blade channel 126 adjacent walls defining the blade channel 126.

The tissue contacting surface 125 of the upper jaw 124 includes a protrusion 156 opposing the blade channel 126 of the fastener cartridge 130. The protrusion 156 extends into the blade channel 126 when the jaws 122, 124 are in the approximated configuration as shown in FIG. 6. The protrusion 156 urges the tissue T into the blade channel 126 and may compress the tissue T into the blade channel 126. As shown, the protrusion 156 has a triangular cross-sectional shape; however, the protrusion 156 may have a variety of shapes that fit within the blade channel 126 of the lower jaw 122 (e.g., semi-circular, rectangular, pentagonal, etc.). When the tissue T is within the blade channel 126, the fasteners 132 are ejected from the fastener cartridge 130 and the ultrasonic blades 154 are activated to cut and seal the tissue T. The protrusion 156 being received within the blade channel 126 may also align the fastener cartridge 130 and the anvil 140.

It is contemplated that the tissue contacting surfaces 123, 125 of the fastener cartridge 130 and the anvil 140 may include buttresses (not explicitly shown) as detailed above to provide additional support to the tissue T as the tissue is stapled and cut. The buttresses may also be welded together adjacent the cutlines of the ultrasonic blades 154 as detailed above.

It is also contemplated that the protrusion 156 may include an ultrasonic blade such that after the tissue T is stapled and sealed, the ultrasonic blade of the protrusion 156 is activated to cut the tissue along a tip 156a of the protrusion 156.

While several embodiments of the disclosure have been shown in the drawings, it is not intended that the disclosure be limited thereto, as it is intended that the disclosure be as broad in scope as the art will allow and that the specification be read likewise. For example, in any of the embodiments disclosed herein, the surgical instrument can include one or more electrosurgical components, such as monopolar or bipolar components for cutting, cauterizing, and/or sealing tissue or buttress material. Any combination of the above embodiments is also envisioned and is within the scope of the appended claims. Therefore, the above description should not be construed as limiting, but merely as exemplifications of particular embodiments. Those skilled in the art will envision other modifications within the scope of the claims appended hereto.

What is claimed:

1. An end effector comprising:
    a first jaw including a fastener cartridge having a first tissue contacting surface and a plurality of fasteners arranged in rows parallel to a longitudinal axis of the first jaw;
    a first buttress attached to the first tissue contacting surface;
    a second jaw including a second tissue contacting surface, the first and second jaws movable relative to one another and configured to grasp tissue therebetween;
    a second buttress attached to the second tissue contacting surface; and
    an ultrasonic blade activatable to weld the first buttress to the second buttress and to subsequently cut the welded first and second buttresses and tissue grasped between the first and second jaws.

2. The end effector according to claim 1, wherein the ultrasonic blade has a first portion disposed on the first tissue contacting surface between two rows of the plurality of fasteners.

3. The end effector according to claim 2, wherein the ultrasonic blade has a second portion disposed on the second tissue contacting surface opposing the first portion of the ultrasonic blade.

4. The end effector according to claim 1, wherein the ultrasonic blade has a second portion disposed on the second tissue contacting surface parallel to a longitudinal axis of the second jaw.

5. The end effector according to claim 1, wherein the plurality of fasteners are ejectable from the fastener cartridge and are configured to secure the first and second buttresses about tissue grasped between the first and second jaws.

6. The end effector according to claim 1, wherein the plurality of fasteners are staples and the second jaw includes an anvil for deforming the staples as the staples are ejected from the fastener cartridge.

7. A method of dissecting tissue, the method comprising:
    clamping tissue between opposing jaws of an end effector, each of the opposing jaws having a buttress attached to a tissue contacting surface;
    ejecting fasteners from one of the opposing jaws through each of the buttresses to fasten the clamped tissue together, the fasteners disposed in rows parallel to a longitudinal axis of the end effector; and
    activating an ultrasonic blade disposed in a blade channel disposed along the longitudinal axis of the end effector to weld the buttresses together and to subsequently cut the tissue and the welded buttresses.

8. The method according to claim 7, wherein clamping tissue between opposing jaws of the end effector includes a protrusion on one jaw urging a portion of the tissue into the blade channel of the opposing jaw.

* * * * *